(12) United States Patent
Pownder et al.

(10) Patent No.: US 7,202,077 B2
(45) Date of Patent: Apr. 10, 2007

(54) METHODS FOR ENHANCING THE TRANSLATION AND EXPRESSION OF RECOMBINANT PROTEINS

(75) Inventors: Tracey A. Pownder, Bellevue, WA (US); Chung Chan, Issaquah, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 10/122,882

(22) Filed: Apr. 12, 2002

(65) Prior Publication Data

US 2003/0228657 A1 Dec. 11, 2003

Related U.S. Application Data

(60) Provisional application No. 60/283,688, filed on Apr. 13, 2001.

(51) Int. Cl.
*C12N 15/00* (2006.01)
*C12N 15/11* (2006.01)
*C12N 1/20* (2006.01)
*C12P 21/06* (2006.01)

(52) U.S. Cl. ............. 435/320.1; 435/69.1; 435/252.31; 435/252.35; 435/252.5; 536/24.1; 536/23.2

(58) Field of Classification Search ............... 435/69.4, 435/69.1, 320.1, 252.33, 252.35; 536/24.1
See application file for complete search history.

(56) References Cited

U.S. PATENT DOCUMENTS

| 5,192,669 A | 3/1993 | Schoner et al. ............. 435/69.4 |
| 5,691,169 A | 11/1997 | Dalbøge et al. ............. 435/69.7 |
| 6,184,356 B1 | 2/2001 | Anderson et al. ............ 530/385 |

FOREIGN PATENT DOCUMENTS

| DE | 3843894 | 12/1988 |
| EP | 0392605 | 10/1990 |

OTHER PUBLICATIONS

Schoner et al, Enhanced Translational Efficiency with Two-Cistron Expression Systems, Methods in Enzymology, vol. 85, pp. 94-103.*

Schoner et al., "Translation of a synthetic two-cistron mRNA in *Escherichia coli*", *Biochemistry* 83:8506-8510, Nov. 1986.

Schoner et al., "Enhanced Translational Efficiency with Two-Cistron Expression System", *Methods in Enzymology* 185:94-103, 1990.

Shine et al., "The 3'-Terminal Sequence of *Escherichia coli* 16S Ribosomal RNA: Complementarity to Nonsense Triplets and Ribosome Binding Sites", *Proc. Nat. Acad. Sci.* 71(4):1342-1346. Apr. 1974.

Thomas et al., "*Excherchia coli* plasmid vectors containing synthetic translational initiation sequences and ribosome binding sites fused with the *lacZ* gene", *Gene* 19:211-219, 1982.

De Smit et al., "Secondary structure of the ribosome binding site determines translational efficiency: A quantitative analysis", *Proc. Natl. Acad. Sci.* 87: 7668-7672, Oct. 1990.

Sprengart et al., "The downstream box: an efficient and independent translation initiation signal in *Escherichia coli*", *The EMBO Journal* 15(3)665-674, 1996.

Etchegaray et al., "Translational Enhancement by an Element Downstream of the Initiation Codon in *Eschetichia coli*", *The Journal of Biological Chemistry* 274(15):10079-10085, Apr. 1999.

Ito et al., "Multiple control of *Escherichia coli* lysyl-tRNA synthetase expression involves a transcriptional repressor and a translational enhancer element", *Proc. Natl. Acad. Sci.* 90:302-306, Jan. 1993.

Makoff et al., "The use of two-cistron constructions in improving the expression of a heterologous gene in *E. coli*", *Nucleic Acids Research* 18(7):1711-1718, 1990.

Pedersen et al., "Removal of N-Terminal Polyhistidine Tags from Recombinant Proteins Using Engineered Aminopeptidases", *Protein Expression and Purification* 15:389-400, 1999.

Pryor et al., "High-Level Expression of Soluble Protein in *Escherichia coli* Using a $His_6$-Tag and Maltose-Binding-Protein Double-Affinity Fusion System", *Protein Expression and Purification* 10:309-319, 1997.

Unizyme Laboratories trade show brochure, 1999.
Unizyme Laboratories product insert, 1999.

* cited by examiner

*Primary Examiner*—Dave Trong Nguyen
*Assistant Examiner*—Maria Marvich
(74) *Attorney, Agent, or Firm*—Robyn Adams

(57) ABSTRACT

The increased use of nucleotide sequence data mining techniques has amplified the demand for efficient methods of producing recombinant proteins in prokaryotic cells. A strategy is provided for enhancing the synthesis of recombinant amino acid sequences by improving translation from expression cassettes in vitro before producing recombinant hosts.

11 Claims, No Drawings

METHODS FOR ENHANCING THE TRANSLATION AND EXPRESSION OF RECOMBINANT PROTEINS

This application is related to Provisional Applications 60/283,688 filed on Apr. 13, 2001. Under 35 U.S.C. § 119(e)(1), this application claims benefit of said Provisional Application.

BACKGROUND OF THE INVENTION

The increased availability and identification of genes from human and other genomes has led to an increased need for efficient expression of recombinant proteins. The expression of proteins in bacteria is by far the most widely used approach for the production of cloned genes. For many reasons, expression in bacteria is preferred to expression in eukaryotic cells. For example, bacteria are much easier to grow than eukaryotic cells. More specifically, the availability of a wealth of sophisticated molecular genetic tools and thousands of mutants make E. coli, as an expression host, extremely useful for protein production. However, the high-level production of functional proteins in E. coli., especially those from eukaryotic sources has often been difficult. Inefficient translation initiation is the most common reason for poor expression (Schoner, B. E., et al., Methods Enzymol.185:94–103, 1990).

Translation initiation depends on the polynucleotide sequence of the ribosomal binding site (RBS), its distance from the initiation codon and the sequence immediately upstream of the initiation codon (Shine J. and Dalgarno L. Proc Natl Acad Sci USA. 71(4):1342–6, 1994; and Thomas D. Y., et al., Gene 19(2):211–9, 1982). However, poor initiation can occur despite the fact that an expression vector contains a good RBS from a highly expressed protein. The presence of a strong RBS along with an appropriately spaced initiation codon does not ensure efficient translation of any particular gene. One variable that continuously changes as recombinant genes are move to different expression vectors is the nucleotide sequence following the initiation codon. In fact, this part of the coding sequence can drastically affect translation. The most accepted explanation for this influence of the beginning of the coding sequence on the initiation of translation involves the absence or presence of secondary polynucleotide structures around the RBS and 5' end of the translated sequence (de Smit M. H., and van Duin J., Proc Natl Acad Sci USA. 87(19):7668–72, 1990).

Recently, it has been reported that the downstream box (DB) polynucleotide sequence, located immediately downstream of the start codon in T7 phage gene 0.3, causes pronounced stimulation of expression when placed upstream of cloned genes, and that this effect is probably due to a stimulation of translation efficiency (Sprengart, M. L., et al., EMBO J. 15(3):665–74, 1996; and Etchegaray, J. P. and Inouye M., J Biol Chem. 274(15):10079–85, 1999). This led to the identification of a DB consensus sequence (SEQ ID NO:4), which was also found in other highly expressed genes such as ribosomal protein, elongation factor and all tRNA synthetases (Ito, K., et al., Proc Natl Acad Sci USA. 90(1):302–6, 1993), suggesting that E. coli. might use this consensus sequence to regulate gene expression. All the identified DB elements display partial complementarity to nucleotide 1467–1481 (SEQ ID NO:5) of the 16S rRNA of E. coli. Mutagenesis analysis has indicated that, increases in the level of complementarity to this region of 16S rRNA led to increased expression. Based on this observation, it has been concluded that DB sequences enhance and stabilize the interactions of the ribosome with mRNAs by base pairing to nucleotide 1467–1481 of 16S rRNA (Ito, ibid).

The two-cistron expression system has been developed to deal with translational initiation problems and has achieved some success (Schoner, B. E., et al., Proc Natl Acad Sci USA. 83(22):8506–10, 1986). This system contains a small well-translated coupler gene followed by a stop codon and then, the gene of interest, which is translated by a re-initiation process. This two-cistron approach can greatly improve the expression of target genes in a plasmid where the RBS is very poor due to inhibitory secondary structure at the 5' end of their mRNA. However, it cannot improve the efficiency of a weak RBS sequence (Makoff, A. J., and Smallwood, A. E., Nucleic Acids Res.18(7):1711–8, 1990).

Despite these advances in the expression of recombinant proteins in bacterial hosts, there exists a need for improved methods for high-level translation initiation and higher yields for protein production.

BRIEF SUMMARY OF THE INVENTION

The present invention provides improved methods for producing peptides, polypeptides, and proteins by recombinant host cells. According to one aspect of the invention, a novel nucleic acid sequence, and a gene of interest are introduced into an expression vector, by way of homologous recombination. The recombined expression vector, containing the novel nucleic acid sequence and gene of interest, is then reintroduced into a prokaryotic host, and the protein encoded by the gene of interest is produced. The production level of the protein is enhanced as compared to production without the novel nucleic acid molecule.

DESCRIPTION OF THE INVENTION

1. Overview

As described herein, the present invention provides methods for increasing protein production by improving the libosome binding site in a new two-cistron expression cassette, which incorporates a novel expression coupler. The expression coupler is devoid of rare codons and potential secondary structures. The new two-cistron expression cassette sequence is able to enhance the yield of poorly expressed heterologous genes in E. coli. Furthermore, this new expression coupler, herein called EC, provides a unique approach for optimizing heterologous protein expression in bacteria.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "structural gene" refers to a nucleic acid molecule that is transcribed into messenger RNA (mRNA), which is then translated into a sequence of amino acids characteristic of a specific polypeptide. A "gene of interest" can be a structural gene.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules with free 5' and 3' ends. Linear DNA can be prepared from closed circular DNA molecules, such as plasmids, by enzymatic digestion or physical disruption.

"Directional ligation" refers to a method of producing a nucleic acid polymer comprising monomers arranged in a fixed orientation. For example, directional ligation can be used to produce a polymer comprising tandem repeats of monomers with head-to-tail orientations.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoters include, for example, but not limited to, IPTG-inducible promoters, bacteriophage T7 promoters and bacteriophage λpL. See Sambrook et al., Molecular Cloning: A Laboratory Manual, 3rd ed., Cold Spring Harbor Laboratory Press, Cold Spring Harbor, N.Y., 2001. A typical promoter will have three components, consisting of consensus sequences at −35 and −10 with a sequence of between 16 and 19 nucleotides between them (Lisset, S. and Margalit, H., *Nucleic Acids Res.* 21: 1512, 1993). Promoters of this sort include the lac, trp, trp-lac (tac) and trp-lac(trc) promoters. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the term "multiple" or "multimeric" refers to two or more copies of a gene of interest, such as 2 to 50 copies, 2 to 30 copies, 2 to 20 copies, 2 to 15 copies, or 2 to 10 copies. Further exemplary ranges include 3 to 20 copies, 3 to 15 copies, or 3 to 10 copies. Conveniently, a construct can comprise 3 or more copies (e.g., 3 to 7, or 5 to 7). Ranges of 7 or more, for example 7 to 30 copies, 7 to 20 copies or 7 to 15 copies, may also be useful.

A "polycistronic transcription unit" refers to a nucleic acid construct in which more than one gene is under the control of the same promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins, colony stimulating factors, interferons, stem cell growth factors, erythropoietin, and thrombopoietin.

An "anti-idiotype antibody" is an antibody that binds with the variable region domain of an immunoglobulin.

An "antibody fragment" is a portion of an antibody such as F(ab')$_2$, F(ab)$_2$, Fab', Fab, and the like. Regardless of structure, an antibody fragment binds with the same antigen that is recognized by the intact antibody.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

A "fusion protein" is a hybrid protein expressed by a nucleic acid molecule comprising nucleotide sequences of at least two genes.

The term "antibody fusion protein" refers to a recombinant molecule that comprises an antibody, or antibody fragment, and a therapeutic agent. Examples of therapeutic agents suitable for such fusion proteins include immunomodulators ("antibody-immunomodulator fusion protein") and toxins ("antibody-toxin fusion protein"). Illustrative toxin components include a *Pseudomonas* exotoxin moiety, a diphtheria toxin moiety, an RNase moiety, a DNase I moiety, a gelonin moiety, and a *Staphylococcal* enterotoxin-A moiety.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

An "antigenic peptide" is a peptide that will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell, which binds or expresses the antigen. The antigenic peptide can be bound in the context of a class I or class II major histocompatibility complex molecule on an antigen presenting cell or on a target cell.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of a Nucleic Acid Molecule Containing an Expression Coupler and a Gene of Interest The present invention provides a novel nucleic acid construct, which is useful for enhanced protein production. One aspect of the invention provides a novel nucleic acid molecule, herein termed an Expression Coupler (EC), which can be genetically inserted upstream of a gene of interest in an expression vector resulting in improved translation of the protein. The insertion of the EC converts the nucleic acid construct into a RNA molecule having at least two cistrons. Within one aspect the present invention provides the polynucleotide sequence of the EC as described, for example, by the following formula: A-B-C-D-E, wherein A is a start codon; B is a polynucleotide sequence of 13 nucleic acids, wherein the polynucleotide sequence has homology to SEQ ID NO:2, wherein at least 5 of the 13 nucleic acids are identical to the corresponding position in SEQ ID NO:2, and wherein the nucleic acid sequence does not code for a stop codon; C is a polynucleotide sequence selected from the group consisting of: a) a polynucleotide sequence having the first 10 nucleic acids of SEQ ID NO:3; b) a polynucleotide sequence having the first 13 nucleic acids of SEQ ID NO:3; c) a polynucleotide sequence having the first 16 nucleic acids of SEQ ID NO:3; and d) a polynucleotide sequence having the first 19 nucleic acids of SEQ ID NO:3; D is the polynucleotide sequence as shown in SEQ ID NO:4; and E is a polynucleotide sequence selected from the group consisting of: SEQ ID NO:5; SEQ ID NO:6; SEQ ID NO:7; SEQ ID NO:8; SEQ ID NO:9; SEQ ID NO:10; SEQ ID NO:11; SEQ ID NO: 12; and SEQ ID NO:13, wherein at least 50% nucleotides are either adenine or thymine; and wherein only E encodes a stop codon. Within an embodiment, the invention provides an expression cassette comprising the isolated nucleic acid molecule of the EC, as described above operably linked to a gene of interest.

Within another aspect, is provided an expression vector comprising a transcription promoter, the expression cassette and a transcription terminator, wherein the promoter is operably linked with the expression cassette, and wherein the expression cassette is operably linked with the transcription terminator. Within an embodiment, the expression vector comprises multiple expression cassettes. Within another embodiment, the the gene of interest encodes an affinity tag. Within another embodiment, is provided a recombinant host cell comprising the expression vector, wherein the host cell is a bacterial cell. Within a further embodiment, the bacterial cell is selected from the group consisting of: *E. coli; Bacillus;* and *Streptomyces*. Within yet a further embodiment, the bacterial cell is *E. coli.*

Within another aspect, the invention provides a method of using the expression vector to produce the protein encoded by the gene of interest, comprising culturing recombinant host cells that comprise the expression vector and that produce the protein. Within an embodiment is provided the EC polypeptide encoded by the EC polynucleotide.

Within another aspect, the invention provides an antibody or antibody fragment that specifically binds with the EC polypeptide.

Within another aspect is provided a method of detecting the presence of EC gene expression in a biological sample, comprising: (a) contacting a EC nucleic acid probe under hybridizing conditions with either (i) test RNA molecules isolated from the biological sample, or (ii) nucleic acid molecules synthesized from the isolated RNA molecules, wherein the probe consists of a nucleotide sequence comprising a portion of the nucleotide sequence of the EC nucleic acid molecule, or complements thereof, and (b) detecting the formation of hybrids of the nucleic acid probe and either the test RNA molecules or the synthesized nucleic acid molecules, wherein the presence of the hybrids indicates the presence of EC RNA in the biological sample, or, (a') contacting the biological sample with an antibody, or an antibody fragment, wherein the contacting is performed under conditions that allow the binding of the antibody or antibody fragment to the biological sample, and b') detecting any of the bound antibody or bound antibody fragment.

Within another aspect is provided a method for producing a nucleic acid construct suitable for expression of an amino acid sequence of interest, comprising inserting the EC polynucleotide between the Shine-Dalgarno sequence of an expression vector and the nucleotide sequence encoding the amino acid sequence of interest. Within an embodiment, the nucleic acid construct comprises multiple copies of the polynucleotide and the amino acid sequence of interest.

Within another aspect, the invention provides a purified polynucleotide comprising the following nucleic acid sequence: A-B-C-D-E wherein: A comprises or consists of a start codon; B comprises or consists of a polynucleotide sequence of 13 nucleic acids, wherein the polynucleotide sequence has homology to SEQ ID NO:2, wherein at least 5 of the 13 nucleic acids are identical to the corresponding position in SEQ ID NO:2, and wherein the nucleic acid sequence does not code for a stop codon; C comprises or consists of a nucleic acid selected from the group consisting of: a) adenine; b) thymine; c) cytosine; and d) guanine; D comprises or consists of the polynucleotide sequence as shown in SEQ ID NO:4; and E comprises or consists of a polynucleotide sequence selected from the group consisting of: SEQ ID NO:5; SEQ ID NO:6; SEQ ID NO:7; SEQ ID NO:8; SEQ ID NO:9; SEQ ID NO:10; SEQ ID NO:11; SEQ ID NO: 12; and SEQ ID NO:13, wherein at least 50% nucleotides are either adenine or thymine; and wherein only E encodes a stop codon. Within an embodiment, C is adenine.

Within another aspect the invention provides a purified polynucleotide comprising the following nucleic acid sequence: A-B-C-D-E wherein: A is a start codon; B is a polynucleotide sequence of 13 nucleic acids, wherein the polynucleotide sequence has homology to SEQ ID NO:2, wherein at least 5 of the 13 nucleic acids are identical to the corresponding position in SEQ ID NO:2, and wherein the nucleic acid sequence does not code for a stop codon; C is a polynucleotide having the nucleic acid sequence of SEQ ID NO:20; D is the polynucleotide sequence as shown in SEQ ID NO:4; and E is a polynucleotide sequence selected from the group consisting of: SEQ ID NO:5; SEQ ID NO:6; SEQ ID NO:7; SEQ ID NO:8; SEQ ID NO:9; SEQ ID NO:10; SEQ ID NO:11; SEQ ID NO: 12; and SEQ ID NO:13, wherein at least 50% nucleotides are either adenosine or thymine; and wherein only E encodes a stop codon.

Within another aspect the invention provides a purified polynucleotide comprising the following nucleic acid sequence: A-B-D-E wherein:

A is a start codon; B is a polynucleotide sequence of 13 nucleic acids, wherein the polynucleotide sequence has homology to SEQ ID NO:2, wherein at least 5 of the 13 nucleic acids are identical to the corresponding position in SEQ ID NO:2, and wherein the nucleic acid sequence does not code for a stop codon; D is the polynucleotide sequence as shown in SEQ ID NO:4; and E is a polynucleotide sequence selected from the group consisting of: SEQ ID NO:5; SEQ ID NO:6; SEQ ID NO:7; SEQ ID NO:8; SEQ ID NO:9; SEQ ID NO:10; SEQ ID NO:11; SEQ ID NO: 12; and SEQ ID NO:13, wherein at least 50% nucleotides are either adenosine or thymine; and wherein only E encodes a stop codon.

Illustrative examples of sequences encompassed by the nucleic acid molecule of the EC are shown in SEQ ID NOs: 1, 18, 19, 21, 22, and 23.

A. Expression Cassette Design

For the purposes of the present invention an expression cassette comprises an Expression Coupler and a gene of interest. The gene of interest can encode any desired amino acid sequence. Exemplary amino acid sequences include proteins, polypeptides, peptides, and fusion proteins. Polypeptides can consist of about 10 to about 20 amino acids, about 20 to about 40 amino acids, about 40 to about 100 amino acids, or greater than 100 amino acids.

Illustrative proteins include antibodies and antibody fragments, receptors, hormones, and other proteins having potential industrial or therapeutic value. For example, an expression cassette can include a nucleic acid molecule that encodes a pharmaceutically active molecule, such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, and IL-17), colony stimulating factors (e.g., granulocyte-colony stimulating factor, and granulocyte macrophage-colony stimulating factor), interferons (e.g., interferons-α, -β, -γ, -ω, -δ, -τ, and -ε), a stem cell growth factor, erythropoietin, and thrombopoietin. Additional examples of a protein of interest include an antibody, an antibody fragment, an anti-idiotype antibody (or, fragment thereof), a chimeric antibody, a humanized antibody, an antibody fusion protein, and the like.

The protein of interest can be produced such that the protein is retained inside the host cell or secreted. When it is desired that the protein is not secreted, the expression cassette can be comprised of a promoter, the EC nucleotide sequence, and the gene of interest. The expression cassette is then introduced into a recombinant host as usual. Alternatively, recombinant host cells can be produced that secrete the desired protein. Accordingly, the present invention contemplates expression cassettes comprising a promoter, the EC nucleotide sequence, a nucleotide sequence encoding a secretory signal sequence (also known as a "signal peptide," a "leader sequence," a "prepro sequence," or a "pre sequence") and the gene of interest. The secretory signal sequence is operably linked to a gene of interest such that the two sequences are joined in the correct reading frame and positioned to direct the newly synthesized protein of interest into the secretory pathway of the host cell. Secretory signal sequences are commonly positioned 5' to the nucleotide sequence encoding the amino acid sequence of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Expression cassettes can also comprise nucleotide sequences that encode a peptide tag to aid the purification of the desired protein. Peptide tags that are useful for isolating recombinant polypeptides include, for example, polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., Arch. Biochem. Biophys. 329:215 (1996), Morganti et al., Biotechnol. Appl. Biochem. 23:67 (1996), and Zheng et al., Gene 186:55 (1997). Nucleic acid molecules encoding such peptide tags are available, for example, from Sigma-Aldrich Corporation (St. Louis, Mo.).

B. Design of Vector Comprising an Expression Cassette

Expression vectors that are suitable for production of a desired protein in prokaryotic cells typically comprise (1) prokaryotic DNA elements coding for a bacterial replication origin and an antibiotic resistance marker to provide for the growth and selection of the expression vector in a bacterial host; (2) DNA elements that control initiation of transcription, such as a promoter; (3) DNA elements that control the processing of transcripts, such as a transcription termination, and (4) a selectable marker gene for prokaryotic cells. As discussed above, expression vectors can also include nucleotide sequences encoding a secretory sequence that directs the heterologous polypeptide into the secretory pathway of a host cell.

In addition, an expression vector suitable for use in the methods described herein will contain an expression cassette having at least one EC and one gene of interest. Similarly, a cassette can include one EC linked to more than one gene of interest. Also, multiple cassettes containing the same or different genes of interest can be incorporated into the expression vector. For example, in one embodiment of the invention, one EC can be inserted between the Shine-Delgarno sequence of the vector and the start codon of a gene of interest. In another embodiment, a second gene of interest can be linked to the first gene of interest. In another embodiment, a first cassette having one EC-gene of interest pair can be followed by a second cassette having a second EC-gene of interest pair. Many combinations of coupling one or more ECs to one or more genes of interest are encompassed by the present invention. Thus a multiplicity of EC/gene of interest cassettes can be inserted into an expression vector such that the expression vector can have between one and ten or more expression cassettes. Thus, many combinations of coupling one or more ECs to one or more genes of intereste are encompassed by the present invention.

One of ordinary skill in the art will be familiar with a multitude of molecular techniques for the preparation of the expression cassette. For example, the EC polynucleotide can be prepared by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications,* White (ed.), pages 263–268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Examples of alternate techniques that can be used to prepare the EC, gene of interest, expression cassette, and/or the expression vector include, for example, restriction endonuclease digestion and ligation, and polymerase chain reaction, all of which are well-known in the art. Addtionally, yeast recombination can be used to prepare the polynucleotides. See U.S. Pat. No. 6,207,442, Plasmid Construction by Homologous Recombination, incorporated herein by reference.

A wide variety of selectable marker genes are available (see, for example, Kaufman, *Meth. Enzymol.* 185:487 (1990); Kaufman, *Meth. Enzymol.* 185:537 (1990)). In the present context, a suitable selectable marker is "titratable," in that the resistance of a cell to a high dose of toxic drug will be related to the number of selectable marker proteins produced by the cell. This characteristic is lacking when the selectable marker is an enzyme that can neutralize a high number of toxic drug molecules per enzyme.

Ble genes, such as the Sh ble gene, are particularly useful selectable marker genes for the presently described methods. These genes produce a protein that inhibits the activity of bleomycin/phleomycin-type drugs, such as ZEOCIN (Gatignol et al., *Mol. Gen. Genet.* 207:342 (1987); Drocourt et al., *Nucl. Acids Res.* 18:4009 (1990)). The protein coded by a bleomycin-resistance gene binds a bleomycin-type drug in a one to one ratio, resulting in a sequestering of the toxic drug (see, for example, Gatignol et al., *FEBS Lett.* 230:171 (1988)). In addition to the stoichiometric binding, another advantage of this system is that ZEOCIN is toxic in a broad range of cell types, including bacteria, fungi, plant, avian, insect, and mammalian cells.

As one skilled in the art would know selectable markers for bacterial expression include markers that confer antibiotic resistance. Antibiotics such as ampicillin, tetracycline, chloramphenicol, and kanamycin are commonly used. An expression vector can carry more than one such antibiotic resistance gene. See also, Sambrook et al., ibid.

Other selectable markers can be used, as well, and in some cases it may be preferable to make use of a selectable marker that does not require the use of an antibiotic. One example of this sort of selectable marker uses the hok/sok system from plasmid R1. The hok gene encodes the toxic Hok protein of 52 amino acids and the sok gene encodes an antisense RNA, which is complementary to the hok mRNA leader sequence. This selectable marker is known to one skilled in the art and is described in more detail by Gerdes, K. et al., *Genetic Engineering,* 19:49–61, 1997.

C. Generation of the Expression Vector

After constructing the expression vector, the vector is propagated in a host cell to synthesize nucleic acid molecules for the generation of a nucleic acid polymer. Vector propagation is conveniently carried out in a prokaryotic host cell, such as *E. coli* or *Bacillus subtilus.* Suitable strains of *E. coli* include BL21(DE3), BL21(DE3)pLysS, BL21(DE3) pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in DNA Cloning: *A Practical Approach,* Glover (ed.) (IRL Press 1985)). Standard techniques for propagating vectors in prokaryotic hosts are well-known to those of skill in the art (see, for example, Ausubel et al. (eds.), *Short Protocols in Molecular Biology,* $3^{rd}$ Edition (John Wiley & Sons 1995) ["Ausubel 1995"]; Wu et al., *Methods in Gene Biotechnology* (CRC Press, Inc. 1997)).

The present invention also includes the production of heteropolymers that comprise expression vectors containing different genes. As an illustration, it may be necessary to transfect cells with genes that encode post-translational processing enzymes for the protein of interest. In this case, linearized expression vectors that include genes for the appropriate enzymes can be ligated to produce a heteropolymer. The processing genes can be controlled by similar regulatory elements. Moreover, the relative amounts of the genes can be controlled by altering the ratios of the various expression vectors. Similarly, heteropolymers can be devised to provide expression of subunits of a multimeric protein, or to provide a recombinant host cell with multiple members of a metabolic pathway, which can modify the properties of the host cell.

4. Production of Recombinant Protein by Host Cells

A nucleic acid polymer, such as an expression vector, can be introduced into host cells using a variety of standard techniques including liposome-mediated transformation, heat shock transformation, microprojectile-mediated delivery, electroporation, and the like. Transformed cells can be selected and propagated to provide recombinant host cells that express the gene of interest.

Standard methods for introducing nucleic acid molecules into bacterial, cells are provided, for example, by Ausubel (1995).

A wide variety of suitable recombinant host cells are encompassed by the present invention and includes, but is not limited to, gram-negative prokaryotic host organims (such as, *E. coli*, for example, *E. coli* K12, *E. coli* K12 RV308, *E. coli* K12 MM294, *E. coli* K12 C600, *E. coli*HB101, *E. coli* K12 C600 R.sub.k-M.sub.k-, *E. coli* K12 RR1, *Serratia, Pseudomonas, Caulobacter*, and the like, as well as gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*.

While the present invention is designed to be used in a recombinant host, one skilled in the art would also know that this system can also be used in a cell-free expression system. A commercially available cell-free translation system is available, for example, from Roche Diagnostics (Rapid Translation System RTS *E. coli* Circular Template Kit; Rapid Translation System RTS 500 Instrument; and Rapid Translation System RTS 100 *E.coli* HY Kit; Roche Diagnostics, Indianapolis, Ind.)

The expression vectors and methods of this invention are used with suitable host cells and standard fermentation techniques and conditions to produce the specific gene of interest, and the recombinant protein is further purified by routine methods from the fermentation broth. In general, see Sambrook et al., Molecular Cloning: *A Laboratory Manual*, 3rd ed., Cold Spring Harbor Laboratory Press, Cold Spring Harbor, N.Y., 2001, Volume three: Chapter 15, pages 15.14–15.54.

Additionally, the EC protein will be useful in monitoring the amount and level of expression of the gene of interest. Using standard methods, one skilled in the art will be able to, upon detection of EC protein, determine the quantity of the gene of interest that is being produced. Such detection of the protein encoded by the EC polynucleotide can be performed by using an antibody produced to the EC protein.

5. Production of Antibodies to EC Proteins

Antibodies to the EC protein may also be useful as a means to monitor the production of the protein of interest.

Antibodies to EC can be obtained, for example, using the product of an EC expression vector. Particularly useful anti-EC antibodies "bind specifically" with EC. Antibodies are considered to be specifically binding if the antibodies exhibit at least one of the following two properties: (1) antibodies bind to EC with a threshold level of binding activity, and (2) antibodies do not significantly cross-react with polypeptides related to EC.

With regard to the first characteristic, antibodies specifically bind if they bind to a EC polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect EC , but not known related polypeptides using a standard Western blot analysis.

Anti-EC antibodies can be produced using antigenic EC epitope-bearing peptides and polypeptides. Antigenic epitope-bearing peptides and polypeptides of the present invention contain a sequence of at least nine, preferably more amino acids encoded by the polynucleotides of the present invention. It is desirable that the amino acid sequence of the epitope-bearing peptide is selected to provide substantial solubility in aqueous solvents (i.e., the sequence includes relatively hydrophilic residues, while hydrophobic residues are preferably avoided).

Polyclonal antibodies to recombinant EC protein or to EC isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning* 2: *Expression Systems, 2nd Edition*, Glover et al. (eds.), page 15 (Oxford University Press 1995). The immunogenicity of a EC polypeptide can be increased through the use of an adjuvant, such as alum (aluminum hydroxide) or Freund's complete or incomplete adjuvant. Polypeptides useful for immunization also include fusion polypeptides, such as fusions of EC or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, goats, or sheep, an anti-EC antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-EC antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol.* 1, pages 2.5.1–2.6.7 (John Wiley & Sons 1991) ["Coligan"], Picksley et al., "Production of monoclonal antibodies against proteins expressed in *E. coli*," in *DNA Cloning* 2: *Expression Systems, 2nd Edition*, Glover et al. (eds.), page 93 (Oxford University Press 1995)).

Briefly, monoclonal antibodies can be obtained by injecting mice with a composition comprising a EC gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-EC antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology, Vol.* 10, pages 79–104 (The Humana Press, Inc. 1992)).

For particular uses, it may be desirable to prepare fragments of anti-EC antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol.* 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11: 1271 (1993), and Sandhu, supra).

As an illustration, a scFV can be obtained by exposing lymphocytes to EC polypeptide in vitro, and selecting antibody display libraries in phage or similar vectors (for instance, through use of immobilized or labeled EC protein or peptide). Genes encoding polypeptides having potential EC polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the EC sequences disclosed herein to identify proteins which bind to EC.

Another form of an antibody fragment is a peptide coding for a single complementarity-determining region (CDR). CDR peptides ("Minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application,* Ritter et al. (eds.), page 166 (Cambridge University Press 1995), and Ward et al., "Genetic Manipulation and Expression of Antibodies," in *Monoclonal Antibodies: Principles and Applications,* Birch et al., (eds.), page 137 (Wiley-Liss, Inc. 1995)).

Alternatively, an anti-EC antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice,* Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-EC antibodies or antibody fragments, using standard techniques. See, for example, Green et al., "Production of Polyclonal Antisera," in *Methods In Molecular Biology: Immunochemical Protocols,* Manson (ed.), pages 1–12 (Humana Press 1992). Also, see Coligan at pages 2.4.1–2.4.7. Alternatively, monoclonal anti-idiotype antibodies can be prepared using anti-EC antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

The present invention, thus generally described, will be understood more readily by reference to the following examples, which are provided by way of illustration and are not intended to be limiting of the present invention.

EXAMPLES

Example 1

Preparation of the Nucleic Acid Construct of the EC and a Gene of Interest

An expression plasmid containing a polynucleotide encoding part of a human gene, herein called IL-20 (zcyto10X1), was inserted behind the EC nucleic acid sequence via yeast homologous recombination as follows: A fragment of IL-20 (zcyto10X1) (SEQ ID NO:14), which was codon-optimized for *E. coli,* was isolated by PCR using a sense primer, ZC 28,770 (SEQ ID NO:15), and an antisense primer, ZC23,993 (SEQ ID NO:16), and a plasmid containing the IL-20 (zcyto10X1) insert as template. The sense primer was designed to contain 41 base pairs corresponding to the EC sequence and 24 base pairs corresponding to the amino terminus of the gene. The antisense primer was designed to correspond to 38 base pairs of the 3' end of the vector which contained the IL-20 (zcyto10X1) insert. The PCR reaction conditions were as follows: 25 cycles of 94° C. for 30 seconds, 50° C. for 30 seconds, and 72° C. for 1 minutes; followed by a 4° C. soak. A small sample (2–4 μl) of the PCR sample was run on a 1% agarose gel with 1×TBE buffer for analysis, and the expected band of approximately 500 bp fragment was seen. The remaining volume of the 100 μl reaction was precipitated with 200 μl absolute ethanol. The pellet was resuspended in 10 μl water to be used for yeast homologous recombination.

One hundred microliters of competent yeast cells (*S. cerevisiae*) were combined with 10 μl of a mixture containing approximately 1 μg of the IL-20 (zcyto10X1) gene, and 100 ng of SmaI digested pTAP186 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol. The yeast were then plated in two 300 μl aliquots onto two -URA D plates and incubated at 30° C.

After about 48 hours, the positive yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform, vortexed for 1 minute, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl $H_2O$.

Example 2

Expression of the Gene of Interest in a Recombinant Host Cell

Transformation of electrocompetent *E. coli* cells (DH12S, Gibco BRL) was done with 1 μl of the yeast DNA prep from Example 1 and 40 μl of DH12S cells. The cells were electropulsed at 2.0 kV, 25 μF and 400 ohms. Following electroporation, 0.6 ml SOC (2% Bacto Tryptone (Difco, Detroit, Mich.), 0.5% yeast extract (Difco), 10 mM NaCl, 2.5 mM KCl, 10 mM MgCl2, 10 mM MgSO4, 20 mM glucose) was added and cells recovered for 1 hour at 37C. The entire transformation was plated in one aliquot on a LB Kan plate (LB broth (Lennox), 1.8% Bacto™ Agar (Difco), 25 mg/L kanamycin).

Individual clones harboring the correct expression construct were identified by expression and PCR. Cells were grown in Superbroth 2 with 30 μg/ml of kanamycin overnight. 50 μl of the overnight culture was used to inoculate 2 ml of fresh in Superbroth 2 with 30 μg/ml of kanamycin. Cultures were grown at 37° C., shaking for 2 hours. One ml of the culture was induced with 1 mM IPTG. Two to four hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 5–10 minutes. Twenty μl were loaded per lane on a 4%–12% PAGE gel (NOVEX). Gels were run in 1×MES buffer. All eight clones screened expressed a band of approximately 17 kD. Clones were also screened via PCR with primers ZC28770 (SEQ ID NO:24) and ZC23993 (SEQ ID NO:25). The PCR reaction conditions were as follows: 25 cycles of 94° C. for 30 seconds, 50° C. for 30 seconds, and 72° C. for 1 minutes; followed by a 4° C. soak. A small sample (2–4 μl) of the PCR sample was run on a 1% agarose gel with 1×TBE buffer for analysis, and the expected band of approximately 500 bp fragment was seen for all eight clones screened. The positive clones subjected to sequence analysis and showed that the EC polynucleotide sequence was correctly inserted upstream of the IL-20 (zcyto10X1) sequence as shown in SEQ ID NO: 17.

Example 3

Removal of the Yeast Origin of Replication from the Nucleic Acid Construct and Expression of the Gene of Interest in Another Recombinant Host The positive clone from Example 2 was digested with Not1/Nco1 (10 μl DNA, 5 μl Buffer 3 (New England BioLabs), 2 μl Not1, 2 μl Nco1, 31 μl water for 1 hour at 37° C.) and religated with T4 DNA ligase buffer (7 μl of the previous digest, 2 μl of 5×buffer, 1 μl of T4 DNA ligase) to remove the yeast sequence, CEN-ARS, and to streamline the vector. The absence of the yeast sequence DNA was confirmed by digestion with Pvu2 and Pst1. The nucleic acid construct was then transformed into *E. coli* W3110s via the protocol listed above for the *E. coli* DH12S.

Induction of cells was done as follows: 37.5 ml of Superbroth 2+kan 30 μg/ml were inoculated with 375 μl of starter culture. Cultures grew at 37° C. for 1 hour and 50 minutes. Twenty-five ml were then induced with 1 mM IPTG and split into two aliquots of 12.5 ml each. One of these aliquots was grown at 37° C. and the other aliquot was grown at 30° C. A negative induction control of 12.5 mls also included. Cultures were harvested at 3 hours post-induction. Two hundred and fifty microliters of culture was mixed with 250 μl glass beads and 250 μl of Thorner Buffer with 5% dye and 5% βME. Samples were vortexed, and then boiled for 5 minutes, and run on a PAGE gel. Twenty μl were loaded per lane on a 4%–12% PAGE gel (NOVEX). Gels were run in 1×MES buffer. Both the 30° C. and the 37° C. cultures expressed a band of approximately 17 kD. The uninduced culture did not.

Several other proteins have been expressed in this manner of inserting the EC upstream of the gene of interest.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A purified polynucleotide comprising the nucleic acid sequence as shown in SEQ ID NO: 1.

2. An expression cassette comprising the nucleic acid molecule of claim 1 operably linked to a gene of interest.

3. An expression vector comprising a transcription promoter, the expression cassette according to claim 2, and a transcription terminator, wherein the promoter is operably linked with the expression cassette, and wherein the expression cassette is operably linked with the transcription terminator.

4. An expression vector comprising a transcription promoter, multiple expression cassettes, and a transcription terminator, wherein the promoter is operably linked with the expression cassettes, and wherein the expression cassettes are operably linked with the transcription terminator, wherein each of the expression cassettes is the expression cassette of claim 2.

5. The expression vector according to claim 3, wherein the gene of interest encodes an affinity tag.

6. A recombinant host cell comprising the expression vector of claim 3, wherein the host cell is a bacterial cell.

7. The recombinant host cell according to claim 6, wherein the bacterial cell is selected from the group consisting of:

a) *E. coil;*
b) *Bacillus;* and
c) *Streptomyces.*

8. The recombinant host cell according to claim 7, wherein the bacterial cell is *E. coli.*

9. A method of producing a protein encoded by the gene of interest, comprising culturing recombinant host cells that comprise the expression vector of claim 3 to produce the protein.

10. A method for producing a nucleic acid construct for expression of a gene sequence of interest, comprising inserting the polynucleotide according to claim 1 between the Shine-Dalgarno sequence of an expression vector and the nucleotide sequence encoding the amino acid sequence of interest.

11. A method of producing a nucleic acid construct for expression of a gene of interest comprising inserting multiple copies of a cassette comprising the polynucleotide of claim 1 and a gene of interest between a transcription promoter and a transcription terminator and wherein the promoter is operably linked with the expression cassettes and wherein the expression cassettes are operably linked with the transcription terminator.

* * * * *

SEQUENCE LISTING

<160> NUMBER OF SEQ ID NOS: 25

<210> SEQ ID NO 1
<211> LENGTH: 51
<212> TYPE: DNA
<213> ORGANISM: Artificial Sequence
<220> FEATURE:
<223> OTHER INFORMATION: Expression Coupler nucleotide sequence

<400> SEQUENCE: 1
atgaaacacc agcatcaaca ccaacatcag caccataagg aggagtagca t      51

<210> SEQ ID NO 2
<211> LENGTH: 13
<212> TYPE: DNA
<213> ORGANISM: E. coli

<400> SEQUENCE: 2
aatcacaaag tgg      13

<210> SEQ ID NO 3
<211> LENGTH: 19
<212> TYPE: DNA
<213> ORGANISM: Artificial Sequence
<220> FEATURE:
<223> OTHER INFORMATION: nucleotides 17 to 35 of SEQ ID NO:1

<400> SEQUENCE: 3
aacaccaaca tcagcacca      19

<210> SEQ ID NO 4
<211> LENGTH: 8
<212> TYPE: DNA
<213> ORGANISM: E. coli

<400> SEQUENCE: 4 taaggagg      8

<210> SEQ ID NO 5
<211> LENGTH: 8
<212> TYPE: DNA
<213> ORGANISM: Artificial Sequence
<220> FEATURE:
<223> OTHER INFORMATION: carboxyl terminus of Expression Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(8)
<223> OTHER INFORMATION: n = A,T,C or G

<400> SEQUENCE: 5 nntagnnn      8

<210> SEQ ID NO 6
<211> LENGTH: 8
<212> TYPE: DNA
<213> ORGANISM: Artificial Sequence

```
<220> FEATURE:
<223> OTHER INFORMATION: alternate carboxyl terminus of Expression
      Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(8)
<223> OTHER INFORMATION: n = A,T,C or G

<400> SEQUENCE: 6 nntaannn                                                                  8

<210> SEQ ID NO 7
<211> LENGTH: 8
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(8)
<223> OTHER INFORMATION: n = A,T,C or G

<400> SEQUENCE: 7 nntgannn                                                                  8

<210> SEQ ID NO 8
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(11)
<223> OTHER INFORMATION: n = A,T,C or G

<400> SEQUENCE: 8
nntagnnnnn n                                                             11

<210> SEQ ID NO 9
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(11)
<223> OTHER INFORMATION: n = A,T,C or G

<400> SEQUENCE: 9
nntaannnnn n                                                             11
```

```
<210> SEQ ID NO 10
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(2)
<223> OTHER INFORMATION: n = A,T,C or G
<220> FEATURE:
<221> NAME/KEY: misc_feature
<222> LOCATION: (6)...(11)
<223> OTHER INFORMATION: n = A,T,C or G

<400> SEQUENCE: 10
nntgannnnn n                                                        11

<210> SEQ ID NO 11
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(5)
<223> OTHER INFORMATION: n = A,T,C or G
<220> FEATURE:
<221> NAME/KEY: misc_feature
<222> LOCATION: (9)...(11)
<223> OTHER INFORMATION: n = A,T,C or G

<400> SEQUENCE: 11
nnnnntagnn n                                                        11

<210> SEQ ID NO 12
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(5)
<223> OTHER INFORMATION: n = A,T,C or G
<220> FEATURE:
<221> NAME/KEY: misc_feature
<222> LOCATION: (9)...(11)
<223> OTHER INFORMATION: n = A,T,C or G

<400> SEQUENCE: 12
nnnnntaann n                                                        11

<210> SEQ ID NO 13
<211> LENGTH: 11
<212> TYPE: DNA
<213> ORGANISM: Artificial Sequence
<220> FEATURE:
<223> OTHER INFORMATION: alternate carboxyl terminus of Expression
      Coupler
<220> FEATURE:
<221> NAME/KEY: misc_feature
<222> LOCATION: (1)...(5)
<223> OTHER INFORMATION: n = A,T,C or G
<220> FEATURE:
<221> NAME/KEY: misc_feature
<222> LOCATION: (9)...(11)
<223> OTHER INFORMATION: n = A,T,C or G
```

-continued

```
<400> SEQUENCE: 13
nnnnntgann n                                                          11

<210> SEQ ID NO 14
<211> LENGTH: 462
<212> TYPE: DNA
<213> ORGANISM: Homo sapiens
<220> FEATURE:
<221> NAME/KEY: misc_feature
<222> LOCATION: (0)...(0)
<223> OTHER INFORMATION: codon optimized for E. coli

<400> SEQUENCE: 14
atgctgaaaa ccctgaacct gggtagctgt gtgatcgcca ccaacctgca ggaaatccgt      60
aacggtttct ctgagatccg tggcagcgtg caggccaaag atggtaacat tgacatccgt    120
atcctgcgtc gtaccgagtc tctgcaggac accaaaccgg cgaaccgttg ctgcctgctg    180
cgccacctgc tgcgtctgta tctggaccgt gttttcaaaa actaccagac cccggaccac    240 tatccctgc gtaaaatcag cagcctggcc aactccttcc tgaccatcaa aaagacctg     300 cgtctgtgtc acgcccacat gacctgccac tgtggtgagg aagcaatgaa aaatacagc    360 cagattctga gccacttcga aaaactggaa ccgcaggcag cagtggtgaa agctctgggt   420
gaactggaca ttctgctgca gtggatggag gagaccgaat ag                     462

<210> SEQ ID NO 15
<211> LENGTH: 65
<212> TYPE: DNA
<213> ORGANISM: Artificial Sequence
<220> FEATURE:
<223> OTHER INFORMATION: Oligonucleotide primer, ZC 28,770

<400> SEQUENCE: 15
atcaacacca acatcagcac cataaggagg agtagcatat gctgaaaacc ctgaacctgg     60
gtagc                                                                65

<210> SEQ ID NO 16
<211> LENGTH: 38
<212> TYPE: DNA
<213> ORGANISM: Artificial Sequence
<220> FEATURE:
<223> OTHER INFORMATION: Oligonucleotide primer, ZC 23,993

<400> SEQUENCE: 16
gtatcaggct gaaaatctta tctcatccgc caaaacac                             38

<210> SEQ ID NO 17
<211> LENGTH: 513
<212> TYPE: DNA
<213> ORGANISM: Artificial Sequence
<220> FEATURE:
<223> OTHER INFORMATION: Fusion of EC and SEQ ID NO:14, codon optimized
      for E. coli

<400> SEQUENCE: 17
atgaaacacc agcatcaaca ccaacatcag caccataagg aggagtagca tatgctgaaa      60
accctgaacc tgggtagctg tgtgatcgcc accaacctgc aggaaatccg taacggtttc    120
tctgagatcc gtggcagcgt gcaggccaaa gatggtaaca ttgacatccg tatcctgcgt    180
cgtaccgagt ctctgcagga caccaaaccg gcgaaccgtt gctgcctgct gcgccacctg    240
ctgcgtctgt atctggaccg tgttttcaaa aactaccaga ccccggacca ctatccctg     300
```

-continued cgtaaaatca gcagcctggc caactccttc ctgaccatca aaaagacct gcgtctgtgt    360 cacgcccaca tgacctgcca ctgtggtgag gaagcaatga aaaatacag ccagattctg    420 agccacttcg aaaaactgga accgcaggca gcagtggtga agctctggg tgaactggac    480 attctgctgc agtggatgga ggagaccgaa tag                                513

<210> SEQ ID NO 18
<211> LENGTH: 42
<212> TYPE: DNA
<213> ORGANISM: Artificial Sequence
<220> FEATURE:
<223> OTHER INFORMATION: Expression Coupler

<400> SEQUENCE: 18
atgaaacacc agcatcaaca ccaacataag gaggagtagc at                       42

<210> SEQ ID NO 19
<211> LENGTH: 51
<212> TYPE: DNA
<213> ORGANISM: Artificial Sequence
<220> FEATURE:
<223> OTHER INFORMATION: Expression Coupler

<400> SEQUENCE: 19
atgaatcaca aagtggatca ccaacatcag caccataagg aggagtagca t             51

<210> SEQ ID NO 20
<211> LENGTH: 4
<212> TYPE: DNA
<213> ORGANISM: Artificial Sequence
<220> FEATURE:
<223> OTHER INFORMATION: nucleotides 1 to 4 of SEQ ID NO: 3

<400> SEQUENCE: 20 aaca                                                                  4

<210> SEQ ID NO 21
<211> LENGTH: 36
<212> TYPE: DNA
<213> ORGANISM: Artificial Sequence
<220> FEATURE:
<223> OTHER INFORMATION: Expression Coupler

<400> SEQUENCE: 21
atgaaacacc agcaccaaca taaggaggag tagcat                              36

<210> SEQ ID NO 22
<211> LENGTH: 33
<212> TYPE: DNA
<213> ORGANISM: Artificial Sequence
<220> FEATURE:
<223> OTHER INFORMATION: Expression Coupler

<400> SEQUENCE: 22
atgaaacacc agcatcataa ggaggagtag cat                                 33

<210> SEQ ID NO 23
<211> LENGTH: 27
<212> TYPE: DNA
<213> ORGANISM: Artificial Sequence
<220> FEATURE:
<223> OTHER INFORMATION: Expression Coupler

<400> SEQUENCE: 23
atgaaacacc ataaggagga gtagcat                                        27

```
<210> SEQ ID NO 24
<211> LENGTH: 65
<212> TYPE: DNA
<213> ORGANISM: Artificial Sequence
<220> FEATURE:
<223> OTHER INFORMATION: Artificial nucleotide ZC 28770

<400> SEQUENCE: 24
atcaacacca acatcagcac cataaggagg agtagcatat gctgaaaacc ctgaacctgg      60
gtagc                                                                 65

<210> SEQ ID NO 25
<211> LENGTH: 38
<212> TYPE: DNA
<213> ORGANISM: Artificial Sequence
<220> FEATURE:
<223> OTHER INFORMATION: Artificial nucleotide ZC23993

<400> SEQUENCE: 25
gtatcaggct gaaaatctta tctcatccgc caaaacac                             38
```